United States Patent
Zingaretti et al.

(10) Patent No.: US 11,191,423 B1
(45) Date of Patent: Dec. 7, 2021

(54) ENDOSCOPIC SYSTEM AND METHODS HAVING REAL-TIME MEDICAL IMAGING

(71) Applicant: DocBot, Inc., Irvine, CA (US)

(72) Inventors: Gabriele Zingaretti, Felton, CA (US); Peter Crosby, San Juan Capistrano, CA (US); Andrew Ninh, Fountain Valley, CA (US); James Requa, Sherman Oaks, CA (US); William E. Karnes, Irvine, CA (US); John Cifarelli, Oyster Bay, NY (US)

(73) Assignee: DocBot, Inc., Irvine, CA (US)

( * ) Notice: Subject to any disclaimer, the term of this patent is extended or adjusted under 35 U.S.C. 154(b) by 0 days.

(21) Appl. No.: 16/931,352

(22) Filed: Jul. 16, 2020

(51) Int. Cl.
| | | |
|---|---|---|
| *G06K 9/00* | (2006.01) | |
| *A61B 1/00* | (2006.01) | |
| *A61B 1/31* | (2006.01) | |
| *A61B 1/01* | (2006.01) | |
| *G06T 7/00* | (2017.01) | |
| *G06N 20/00* | (2019.01) | |
| *G06T 1/60* | (2006.01) | |

(52) U.S. Cl.
CPC .............. *A61B 1/0005* (2013.01); *A61B 1/01* (2013.01); *A61B 1/31* (2013.01); *G06N 20/00* (2019.01); *G06T 1/60* (2013.01); *G06T 7/0016* (2013.01); *G06T 2207/10068* (2013.01); *G06T 2207/30028* (2013.01)

(58) Field of Classification Search
CPC ............ G06T 2207/30032; G06T 2207/30028
See application file for complete search history.

(56) References Cited

U.S. PATENT DOCUMENTS

| 4,915,435 | A | 4/1990 | Levine | |
|---|---|---|---|---|
| 6,082,799 | A | 4/2000 | Marek | |
| 6,928,314 | B1* | 8/2005 | Johnson | ................... G06T 15/08 |
| | | | | 128/920 |
| 7,011,625 | B1* | 3/2006 | Shar | .......................... G06T 7/62 |
| | | | | 382/128 |
| 8,165,358 | B2* | 4/2012 | Sirohey | ................... G06T 19/00 |
| | | | | 382/128 |
| 10,671,934 | B1 | 6/2020 | Ninh et al. | |

(Continued)

OTHER PUBLICATIONS

Anderson, et al., Prepared by ASGE Standards of Practice Committee, Endoscopy by Nonphysicians, *Gastrointestinal Endoscopy*, 69(4):767-771 (2009).

(Continued)

*Primary Examiner* — Avinash Yentrapati
(74) *Attorney, Agent, or Firm* — Eversheds Sutherland (US) LLP; Nicola A. Pisano; Albert K. Heng

(57) ABSTRACT

Systems and methods for improving endoscopy procedures are described that provide not only a conventional real time image of the view obtained by an endoscope, but in addition, a near real time 3D model and/or a 2D flattened image of an interior surface of an organ, which model and image may be processed using AI software to highlight potential tissue abnormalities for closer examination and/or biopsy during the procedure. A navigation module interacts with other system outputs to further assist the endoscopist with navigational indicia, e.g., landmarks and/or directional arrows, that enhance the endoscopists' spatial orientation, and/or may provide navigational guidance to the endoscopist to assist manipulation of the endoscope.

20 Claims, 4 Drawing Sheets

(56) References Cited

U.S. PATENT DOCUMENTS

| | | | |
|---|---|---|---|
| 2003/0132936 A1* | 7/2003 | Kreeger | G06T 7/0012 |
| | | | 345/420 |
| 2004/0249670 A1 | 12/2004 | Noguchi et al. | |
| 2005/0036668 A1 | 2/2005 | McLennan et al. | |
| 2005/0117787 A1* | 6/2005 | Iordanescu | G06T 7/155 |
| | | | 382/128 |
| 2007/0003131 A1* | 1/2007 | Kaufman | G06T 15/08 |
| | | | 382/154 |
| 2007/0005795 A1 | 1/2007 | Gonzalez | |
| 2007/0103464 A1* | 5/2007 | Kaufman | G06T 7/0012 |
| | | | 345/424 |
| 2007/0265492 A1 | 11/2007 | Sonnenschein et al. | |
| 2007/0279521 A1 | 12/2007 | Cohen | |
| 2008/0058593 A1* | 3/2008 | Gu | G06T 5/006 |
| | | | 600/109 |
| 2009/0063118 A1* | 3/2009 | Dachille | G06F 16/5862 |
| | | | 703/11 |
| 2010/0215226 A1* | 8/2010 | Kaufman | G06T 7/0012 |
| | | | 382/128 |
| 2011/0301447 A1* | 12/2011 | Park | G06T 7/0016 |
| | | | 600/407 |
| 2012/0320088 A1 | 12/2012 | Ihara et al. | |
| 2013/0170726 A1* | 7/2013 | Kaufman | G06T 3/0068 |
| | | | 382/131 |
| 2014/0031677 A1 | 1/2014 | Iftimia et al. | |
| 2015/0260534 A1 | 9/2015 | Shen | |
| 2015/0282749 A1 | 10/2015 | Zand et al. | |
| 2015/0374210 A1 | 12/2015 | Durr et al. | |
| 2016/0210411 A1 | 7/2016 | Mentis | |
| 2016/0364526 A1 | 12/2016 | Reicher et al. | |
| 2019/0238791 A1 | 8/2019 | Ingle | |
| 2019/0289359 A1 | 9/2019 | Sekar et al. | |
| 2019/0370963 A1 | 12/2019 | Chiu et al. | |

OTHER PUBLICATIONS

Corley, et al., Adenoma Detection Rate and Risk of Colorectal Cancer and Death, *New England Journal of Medicine*, 370:1298-306 (2014).

Day, et al., Non-Physician Performance of Lower and Upper Endoscopy: A Systematic Review and Meta-Analysis, Endoscopy: A Systematic Review and Meta-Analysis, *Endoscopy*, 46:401-410 (2014).

Greenwald, et al., Mobile Screening Units for the Early Detection of Cancer: A Systematic Review, *Cancer Epidemiol. Biomarkers Prev.*, 26(12):1679-94 (2017).

Kaminski, et al., Quality Indicator for Colonoscopy and the Risk of Interval Cancer, *New England Journal of Medicine*, 362:1795-803 (2010).

Karnes, et al., Su1642 Automated Polyp Detection Using Deep learning: Leveling the Field, *Gastrointestinal Endoscopy*, 85(5), Supplement, AB376-AB377 (2017).

Komaravolu, et al., Colonoscopy Utilization in Rural Areas by General Surgeons: An Analysis of the National Ambulatory Medical Care Survey, *Am. J. Surg.*, 218(2):281-287 (2019).

Riegert, et al., Experience of a Nurse Practitioner Performing Colonoscopy at a Tertiary Center in the United States, *J. Gastrointest. Dig. Syst.*, 5:3 (2015).

Talukdar, et al., Making Endoscopy Mobile: The Journey, *Digestive Endoscopy*, 24 (Suppl. 1): 172-174 (2012).

Urban, et al., Deep Learning Localizes and Identifies Polyps in Real Time With 96% Accuracy in Screening Colonoscopy, *Gastroenterology*, 155(4):1069-1078 (2018).

Wang, et al., Real-Time Automatic Detection System Increases Colonoscopic Polyp and Adenoma Detection Rates: A Prospective Randomized Controlled Study, *Gut*, 68:1813-1819 (2019).

Zachariah, et al., Can Artificial Intelligence (AI) Achieve Real-Time Reset and Discard Thresholds Independently of Device of Operator?, *American Journal of Gastroenterology*, 113:S129 (2018).

Zachariah, et al. Artificial Intelligence for Colon Polyp Detection: Why Should We Embrace This? *Techniques and Innovations in Gastrointestinal Endoscopy*, 22:48-51 (2020).

\* cited by examiner

ENDOSCOPIC SYSTEM AND METHODS HAVING REAL-TIME MEDICAL IMAGING

FIELD OF THE INVENTION

The present invention relates generally to the field of real-time 3 dimensional (3D) reconstructed and 2D flattened imaging of a body cavity, with particular application to endoscopy such as colonoscopy.

BACKGROUND OF THE INVENTION

Endoscopy refers to a medical procedure in which an instrument is used for visual examination of an internal body part. A common example of endoscopy is colonoscopy, during which a flexible tube with imaging apparatus at the distal end is inserted into a person's colon. The purpose of colonoscopy is to search for and identify abnormalities in the internal wall of the colon and, in some cases, remove them. Such abnormalities include polyps and various types of adenomas.

Screening colonoscopy remains the best-proven method to detect and prescribe early treatment for colon cancer. Clinical guidelines typically suggest that a first colonoscopy be performed at age 50. In screening colonoscopy, the colonoscopist performs a rigorous visual examination of the entire internal lining of the colon, looking for abnormalities such as polyps and adenomas. Polyps within certain parameters are often removed during the same procedure.

Colonoscopy typically is performed by a fellowship-trained gastroenterologist. Colonoscopy is also performed by primary care physicians (PCP), general surgeons, nurse practitioner and physician assistants. In this disclosure, each person performing a colonoscopy is referred to as an endoscopist.

A well-accepted measure of quality of a colonoscopy is the so-called "adenoma detection rate" (or ADR). This is a measure of the proportion of patients receiving a colonoscopy in whom an adenoma is detected. ADR is a proven measure of risks of colorectal cancer between screenings ("interval colorectal cancer") and the ADR is inversely associated with the risks of interval cancer. See, Kaminski M. F. et al., "Quality Indicator for Colonoscopy and the Risk of Interval Cancer," NEJM 362:1795-803 (2010).

The prevalence of adenomas in the screening age population is thought to be about 50% (i.e.: half of people screened have at least one adenoma), but typical ADR is about 25%, as reported in Corley D. A. et al "Adenoma Detection Rate and Risk of Colorectal Cancer and Death" NEJM 370:1298-306 (2014). The current ADR rate of 25% means that in half of screened patients an adenoma is missed.

There are several factors that contribute to lower than ideal ADR. One factor is the difficulty of identifying a polyp or adenoma, even though it may be in the visual field of the colonoscopy image.

Another factor that contributes to the lower than ideal ADR is the difficulty of ensuring that the entire internal surface of the colon has been imaged. It is difficult for a colonoscopist to remember what has been imaged, and "integrate" those images mentally to conclude that the entire internal surface has been examined. Thus, it is challenging for the endoscopist to ensure that the entire internal surface of the colon has been visualized. Failure to visualize the entire internal surface poses a risk of missing potentially harmful polyps or cancers. On average, only about 81% of the colon mucosa is visualized in a colonoscopy under optimal conditions, as reported in Eddakanambeth, V J, Enders, F, Tavanapong, W, Oh, J, Wong, J, de Groen, P C. "Colonoscopy what endoscopists inspect under optimal conditions." Digestive Disease Week 2011, Chicago, Ill.

One of the challenges of endoscopy, particularly colonoscopy, is that the endoscopist views the structure of interest in real time with only a forward-looking view from the tip of the endoscope. That arrangement provides no registration of the image to the overall anatomy and offers few visual clues for orientation or location. Moreover, the colon is a constantly moving organ that lacks rigid boundaries, so insertion of a colonoscope can cause changes in the shape and configuration of the colon. Further, the folds in the wall of the colon are constantly moving, thus making it very difficult for an endoscopist to ensure that every fold, nook and cranny is visualized during an examination.

Yet another challenge in endoscopy is that the tip of the endoscope is controlled by a series of knobs and switches located on the hand piece manipulated by the endoscopist. During an examination, the endoscopist looks at the screen (or monitor) and not the controls. Accordingly, it is quite difficult for many endoscopists, especially those for whom endoscopy is not part of their daily practice, to translate the image on the screen into necessary hand movements to re-direct the tip of the endoscope. Hence, control reference between the tip of the endoscope and the controls on the hand piece may be difficult to maintain.

Previously known systems and methods exist for generating 3D volume reconstruction to assist visualizing anatomical bodies as an alternative to scrolling through a series of 2-dimensional (2D) images. Historically, such 3D volume reconstruction, e.g., as used in radiology, relies on stacking 2D images obtained by a medical imaging modality such as MRI, CAT scan, Ultrasound, PET/CT or tomographic synthesis. The images, also called slices, are stitched (or combined) together with specialized software that performs volume rendering, surface rendering, and maximum intensity projection.

The 3D reconstruction resulting from a series of 2D images taken at a certain time provides a 3D anatomical snapshot of a patient's anatomy. One benefit of the process is that the volumes may be color coded with ease, moved, zoomed or stretched to more closely resemble the anatomy physicians and radiologists are accustomed to viewing. For example, a virtual 3D gastrointestinal tract generated from sequential 2D images acquired by a wireless capsule or pill cam is described in Fan Y., Meng M. Q., and Li, B. "3D Wireless reconstruction of wireless capsule endoscopy images" $32^{nd}$ Annual Conf of IEEE EMBS, August 2010.

A limitation of the foregoing approach is that the image presented to the clinician involves interpolation and extrapolation of data from a true imaging modality, resulting in loss of resolution, features and formal correctness. Moreover, through-body imaging modalities, such as X-ray, CT scanning and MRI have fundamental resolution limits such that small features may be missed. In general, these historical approaches employ "post processing" of images after an examination is completed, and cannot provide real time information while the clinician is performing the examination.

In addition, such previously known 3D reconstructions lack registration with the actual anatomy, and thus cannot provide precise positional information for a later-performed procedure. For example, a clinician performing a procedure while viewing a 3D reconstruction generated during a prior examination, typically will find the live anatomy to be distorted, moved, squished and/or stretched compared to the prior 3D reconstruction. This lack of temporal continuity is a significant limitation of existing methods of 3D reconstruction of anatomy.

Previously known methods also have explored providing registration between a stored 3D image and a real time visual field of view. For example, fiducial markers created using gamma radiation have been proposed to provide some level of registration, but that technique exposes a patient to an additional dose of gamma radiation, which is itself potentially harmful, as described, for example, in Kleiman N J, Macvittie T J, Aleman B M, Edgar A B, Mabuchi K, Murihead C R, Shore R E, Wallace W H. "ICRP publication 118: ICRP statement on tissue reactions and early and late effects of radiation in normal tissues and organs: Threshold doses for tissue reactions in a radiation protection context." Am. IRCP. 2012 February; 41(1-2):1-322.

3D volume rendering and reconstruction also has been proposed to develop a "virtual colonoscopy" using raw data from CAT or MRI scan. Although that approach has some value, it includes all of the foregoing mentioned limitations, including low resolution and difficulty in finding an identified area during a later examination. Moreover, a typical colonoscopy procedure combines imaging with an ability to remove identified polyps during the procedure. If a polyp to be removed is identified on virtual colonoscopy, then at least one additional procedure is required to remove the polyp, and finding the corresponding area often is challenging for all of the reasons mentioned above.

It also has been proposed to employ 3D virtual colonoscopy to train a machine learning algorithm for polyp detection in optical colonoscopy (OC), with limited success, as described in Nadeem, S., and Kaufman, A. "Computer-Aided Detection of Polyps in Optical Colonoscopy Images." SPIE Medical Imaging, 2016. As noted by those authors, "It is hard to use machine learning algorithms with OC data since it is not feasible to build the dictionary with OC images and precise depth information." Accordingly, it would be advantageous to provide systems and methods that could overcome the drawbacks described in that article.

U.S. Pat. No. 8,064,669 to Higgins et al and U.S. Pat. No. 8,675,935, also to Higgins, describe systems that use a reference CT scan of an airway to provide an initial reference for developing an evolving 3D reconstruction of the airway as a bronchoscope is advanced through a patient's airways. Those patents do not describe how to solve the problems highlighted above, nor do they suggest systems or methods for generating an evolving 3D or flat 2D image without reference to a prior set of images.

One reported idea to enhance machine learning proposed use of a deep learning and convolutional neural network approach to depth estimation. See, Mahmood, D. and Dun, N. "Deep Learning and Conditional Random Fields-based Depth Estimation and Topographical Reconstruction from Conventional Endoscopy" Med Image Anal. 2018; 48:230-243. However, the approach described in that article suffers from the limitation that it is trained on synthetic data from a physical model, not real-world images, and then validated on a porcine colon but with CT registration. The resulting system algorithms are neither independent nor capable of providing real time information.

3D reconstruction of the colon from consecutive 2D images also has been described using a variety of methods. For example, Hong et al in "3D Reconstruction of virtual colon structures from colonoscopy images" Computerized Medical Imaging and Graphics 2014; 38:22-23, describe several techniques for such reconstruction, including stereo matching, shape-from-texture, shape-from-shading and shape-from-motion. That work utilizes depth from intensity reconstruction in a post-processing environment. Such 3D colon reconstruction techniques cannot be used during a procedure, and so do not address the problems sought to be addressed by this disclosure.

U.S. Pat. No. 8,300,047 to Sudarsky et al describes a mathematical technique for unfolding a 3D reconstruction of the image dataset of a colon obtained from virtual colonoscopy to enable easier viewing. That patent does not teach a method or system for performing the same function on images obtained in real time to provide guidance to an endoscopist during an optical colonoscopy procedure.

Another challenge of colonoscopy involves detection of polyps and other features in real time. U.S. Pat. No. 9,747,687 to Tajbakhsh et al teaches a polyp detection system and method that uses feature extraction of an image appearance around the boundary of a polyp to determine the presence or absence of a polyp. That patent does not address any of the issues of 3D reconstruction, creation of a 2D flat image, or real time registration discussed above.

Previously known systems and methods also have sought to use artificial intelligence (AI) to enhance detection of polyps in real-time with high accuracy during screening colonoscopy, as described in Urban, G., et al "Deep Learning Localizes and Identifies Polyps in Real Time with 96% Accuracy in Screening Colonoscopy" Gastroenterology 2018; 155(4):1069-1078). One such approach is described in commonly assigned U.S. Pat. No. 10,671,934, which is hereby incorporated by reference in its entirety. Such an approach has been shown in clinical studies to provide improved ADR without increasing time and cost, as described in Wang P., et al "Real-Time Automatic Detection System Increases Colonoscopic Polyp and Adenoma Detection Rates: A Prospective Randomized Controlled Study" Gut 2019; 68:1813-1819.

In addition, previously known systems and methods have attempted to generate a two-dimensional map of the internal colon surface to enhance conventional colonoscopy. For example, as described in Armin M A, Barnes N, Grimpen F and Salvado O "Learning colon centreline from optical colonoscopy, a new way to generate a map of the internal colon surface." Healthcare Technology Letters 2019; 6:187-190, the colon centerline may be used to orient the optical images presented to the clinician. Additional efforts have been made to generate a surface reconstruction from endoscopy image sequences, as described in Bergen, T. and Wittenberg T. "Stitching and Surface Reconstruction from Endoscopic Image Sequences: A Review of Applications and Methods." IEEE J Biomed Health Inform 2016; 20:304-21.

U.S. Patent Application Publication No. 2015/0221116 to Wu et al describes a method for stitching together consecutive images acquired through capsule endoscopy. That publication describes how to perform the method as post processing on a large dataset of acquired images, but does not suggest how to use that method on a real-time video feed obtained from optical colonoscopy, or even if such method could be applied to that situation.

Similarly, U.S. Patent Application Publication No. 2017/0046833 to Lurie et al, entitled "3D Reconstruction and Registration of Endoscopic Data," describes a similar post-processing approach for optical colonoscopy images. Once again, that publication does not describe how, or even whether, the disclosed method could be applied in real time to a video feed from an optical colonoscope procedure.

U.S. Patent Application Publication No. 2008/0058593 to Gu and Wolters describes a system and method for analyzing colonoscopy video images, discarding poor quality frames, and then using "glint detection" to register overlapping frames to thereby create a 3D reconstruction of the colon. Glint detection is a term used to describe the features of reflections from the surface of the colon that are shiny (glinting).

Real-time 3D reconstruction of a colon surface using a deep-learning driven system has been described by Ma et al in "Real-Time 3D Reconstruction of Colonoscopic Surfaces for Determining Missing Regions" in Shen D. et al. (Eds) Medical Image Computing and Computer Assisted Intervention—MICCAI 2019. MICCAI 2019. Lecture Notes in Computer Science, vol 11768 (2019). That system uses Simultaneous Localization and Mapping (SLAM) techniques to visualize the internal surface of the colon, and to predict missing areas. The authors noted that their system is only able to work in "chunks" because the system fails on large camera motions or deformation. The disclosed system accordingly is not amenable to reconstruction on withdrawal of the colonoscope, the most important part of a colonoscopy examination for visualizing and detecting polyps and adenomas.

None of the previously known systems or methods enable generation of a simultaneous (or near simultaneous) 3D reconstruction of a colon for navigation at the same time as generation of a simultaneous (or near simultaneous) flat 2D image of the internal surface of the colon for confirmation of visualization of the whole internal surface, to be displayed while the endoscopist is viewing the real-time image of the colon. In addition, no previous system or method provides for an overlay on such images of AI detected features of interest, such as polyps.

In view of the foregoing, it would be advantageous to have a system in which the endoscopist can view a conventional optical image of an internal surface of the colon, while at the same time having access to a 3D reconstruction of the colon. Such as feature would be of assistance in colonoscopy navigation, and in particular, to assist in answering the question "where in the colon is the image now?" It would also be helpful to have an incrementally generated image of the internal surface of the colon unrolled and flattened. Such as feature could highlight areas already visualized, and those areas not yet visualized, thus enabling the endoscopist to confirm that every part of the colon has been visualized. In this disclosure, an unrolled and flattened image is referred to as a flat 2D image. This proposed capability would augment existing endoscopic procedure rather than replace conventional procedure.

Colonoscopy is a procedure performed periodically based on the patient's risk. For example, if a screening colonoscopy performed at the age of 50 finds no polyps, then the physician likely will recommend the next screening colonoscopy after an additional 10 years. On the other hand, if one or more pre-cancerous polyps are found and removed, a next follow up screening colonoscopy is likely to be recommended to be in 5 years or less. If cancerous polyps are identified and removed, the next follow up colonoscopy may be recommended as soon as one year later or less.

It therefore would be advantageous if a colonoscopist could retrieve and view a stored 3D image and flat 2D image of a prior examination while performing a follow-up colonoscopy. In this manner, the colonoscopist could ensure that areas of the colon that were examined during the previous colonoscopy are re-examined during the current examination, thereby lowering the risk of missing vital clues to a potential cancer.

Accordingly, there is a need for systems and methods that show a real-time generated 3D reconstruction of the colon during the procedure, and for recording a 3D image of the colon for reference at a later follow up. In addition, there is a need for a system capable of incrementally developing a flat 2D image of the colon during a procedure, and for recording the flat 2D image for reference at a later colonoscopy follow up.

SUMMARY OF THE INVENTION

In accordance with the principles of the present invention, endoscopy systems and methods are provided that present to an endoscopist an evolving 3D model of the anatomy in near real time as the endoscopic procedure is performed. In particular, the systems and methods employ a 3D reconstruction software module that provides near real time updated 3D model as the anatomy is distorted, compressed and manipulated by the endoscopist. In accordance with one aspect of the invention, the system further comprises a conformal mapping module that generates an "unfolded" 2D flat image of the entire internal surface of the anatomy as the procedure proceeds. While this disclosure describes an exemplary system for colonoscopy, it will be appreciated by a person of skill in the art that the inventive features may be applicable to other forms of endoscopy. Accordingly, the term endoscope and colonoscope are used interchangeably in this disclosure.

In accordance with a further aspect of the invention, the 2D flat image and image of the 3D model of the colon presented to the endoscopist display and highlight features identified by an artificial intelligence model that implements a machine learning ("AI") polyp detection system, thereby giving the endoscopist a holistic view of the location in the colon of polyps that have been detected. The artificial intelligence module also may be programmed to highlight for the endoscopist areas of the internal volume that may be overlooked during imaging. Further, a navigational module may use as inputs the output of any of the 3D reconstruction module, the conformal mapping module, and/or the artificial intelligence module to generate navigational indicia that enable the endoscopist to go back and further image any missing parts. In this manner, the inventive system ensures that the entire volume and surface area has been examined, contributing to the quality of colonoscopy and a likely increase in ADR.

A still further inventive feature of the inventive system is a storage and indexing module that provides the ability to record and store the 3D model and the flat 2D image of the target organ generated during an examination. These stored models and images may be recalled at later, for example, during a subsequent endoscopic procedure, to provide a comparison of the evolution of the anatomy. For example, processing of "before" and "after" 3D models or 2D images may take the form of an overlay of the current model or image to the previous model or image, such that the formation of polyps or adenomas are highlighted. In addition, having a prior reconstruction and 2D flat image available that identifies the location of previous polyps or biopsies will assist in focusing the endoscopist's attention to such areas during the subsequent procedure.

In a preferred embodiment, the system includes multiple display windows, preferably at least two. A first window presents real time images generated by the endoscope as the procedure is being performed, as is conventional for colonoscopy. The first window may include an overlay of information generated by the artificial intelligence module, e.g., that automatically detects for polyps and other features in the real-time images. A second window preferably displays at least one of an image of an evolving 3D model and/or a 2D flat image of the anatomy as the procedure is ongoing. In the context of this disclosure, an "evolving" 3D model or 2D flat image is incrementally generated as the endoscope is advanced (or retracted) within a target organ. Preferably, the first and second windows are presented on separate video monitors, although they could be combined into a single video monitor using picture-in-picture technology. The 3D model and 2D flat image also could be displayed using separate windows. Rendering of the windows may be performed in a parallel or in a multi-threaded process. Parallel processing allows the system to display the video data received from the endoscope in real-time, and also display the graphical indications in the second window at a frame rate that may be lower than or equal to the frame rate of the first window. A fourth window of the monitor also may provide patient related information.

In operation, as an endoscopist performs a colonoscopy procedure using the inventive system and methods, a 3D model of the colon is updated in near real time, so that the endoscopist may use the image of the 3D model as a navigational guide. A storage and indexing module may store the 3D model in a mass storage device at the conclusion of the procedure to provide a visual 3D history of the procedure. In this disclosure, the phrase "near real time" means that a lag between display of the image from the colonoscope and display of the image of the 3D model generally is less than about 15 seconds, and more preferably, less than about 5 seconds. A 2D flat image of the colon also is updated and displayed in near real time, preferably simultaneously with the image of the 3D model, thereby providing a visual guide to the entire internal surface of the colon that highlights any areas that may have been missed.

Because the images provided during a colonoscopy provide limited anatomical guidance, it is not uncommon for the endoscopist to become spatially disoriented within the anatomy during a procedure. Moreover, when this occurs, it is often possible to orient the endoscope in ways that become physically challenging to unwind, thereby resulting in longer procedure times, patient discomfort and added cost. Accordingly, in one embodiment, the system includes a navigation module that overlays the real time video image and/or the image of the 3D model with navigational indicia, for example, a graphical representation of the location and orientation of the tip of the endoscope in real time and/or directional arrows for suggested movement of the endoscope, to aid in orientation and navigation.

Still further, in all endoscopy procedures, endoscopist is required to view the anatomy as if through a tunnel, thus making the procedure very complicated, tiring and prone to missing important features. The 2D flat image of the anatomy provided in near real time on the second display window also may be analyzed by the artificial intelligence model to resolve such issues and enhance ADR detection.

Further features of the invention will become apparent from the detailed description, the claims, and the drawings, which are intended for illustration only and are not intended to limit the scope of the disclosure.

DETAILED DESCRIPTION OF THE INVENTION

The present invention provides systems and methods for improving endoscopy procedures by enhancing the endoscopists' viewing, navigation and interpretation of the interior surface of an organ being examined. In this disclosure, an exemplary system is described for performing colonoscopy, wherein the system provides not only a conventional real time image of the view obtained by the colonoscope, but in addition, a near real time 3D model of the colon and/or a 2D flat image of the interior surface of the colon. In accordance with one aspect of the invention, the real time 3D model and/or 2D image are processed using AI software, which highlights potential features, e.g., polyps or potential adenomas, for closer examination and/or biopsy during the procedure. A navigation module interacts with other system outputs to further assist the endoscopist with navigational indicia, e.g., landmarks and/or directional arrows, that enhance the endoscopists' spatial orientation, and/or may provide guidance to the endoscopist on how to manipulate the endoscope.

In accordance with another aspect of the invention, the systems and methods may employ a storage and indexing module to record and store the 3D model and 2D flat image generated during a procedure in a mass storage device, for later recall and review. Such stored data may be retrieved during a subsequent examination and overlaid with a currently constructed 3D model and 2D flat image to permit comparison. The overlaid models and images also may be processed using AI software, and any changes in the models may be highlighted and displayed during the current procedure to inform the endoscopist of potential areas requiring scrutiny.

In the following specification, reference is made in detail to specific embodiments of the invention suitable for use in endoscopic procedures such as colonoscopy. It should be understood, however, that the benefits and advantages of the present invention are equally available for other endoscopic procedures such as esophageal and airway examination.

Figure 1:
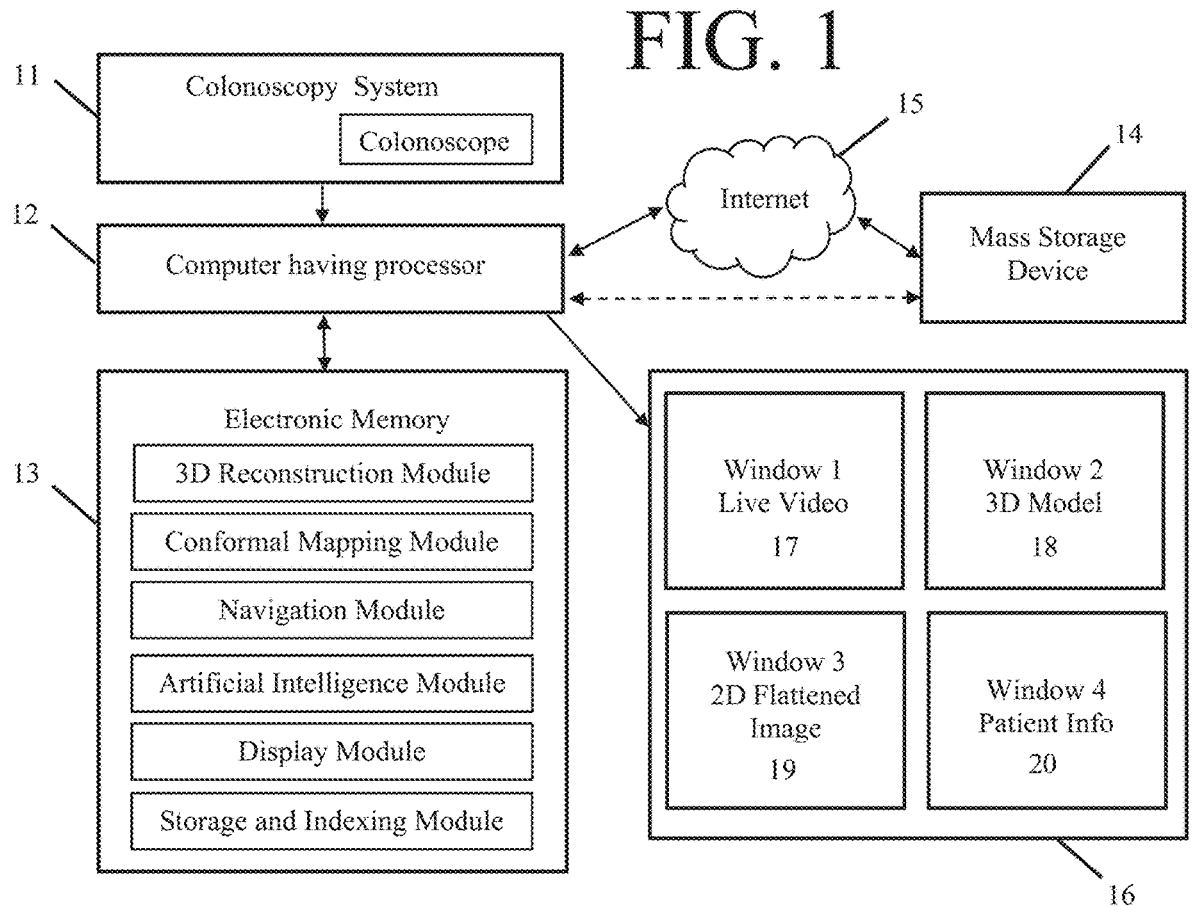
FIG. 1 depicts an exemplary configuration of the system of the present invention.

Referring to FIG. 1, an exemplary embodiment of the inventive system and methods of use is described. The system illustratively comprises colonoscopy system 11, computer 12, electronic memory 13 and display 16. The system may store data in, and recall data from, mass storage device 14 via a local area network (dotted line) or via the cloud, e.g., Internet. Colonoscopy system 11 includes a colonoscope and is used to generate a real-time video stream from within the colon of a patient, when manipulated therein by an endoscopist. Data from colonoscopy system 11, including the real-time video stream, is provided to computer 12, where it is processed using programmed instructions stored in electronic memory 13. The results of processing the real time video stream are sent to display device 16 for viewing in various windows by the endoscopist. As described herein, exemplary embodiments of computer 12 are programmed with software modules that perform multiple tasks, including (1) a 3D reconstruction module that generate a 3D model of the colon; (2) a conformal mapping module that generates a unrolled 2D flat image of the interior surface of the colon; (3) a display module that renders an image of the 3D model/2D flat image for presentation to the endoscopist to assist the endoscopist in examining the colon interior surface; (4) a navigation module that provides spatial orientation and directional guidance to the endoscopist; (5) an artificial intelligence module that analyzes the image stream to identify and highlight potential polyps or potential adenomas in the images; and optionally, (6) a storage and indexing module for storing the 3D model and/or 2D flat image for later recall.

In one preferred embodiment, display 16 includes video window 17, which displays a real-time image of the colonoscope video stream, preferably including an overlay on the video depicting areas of interest detected by the artificial intelligence module, such as polyps. Video window 18 displays a real time or near live image of the 3D model of the colon. Video window 3 displays a real time or near live 2D flat image of the interior surface of the colon, or alternatively, the 2D flat image also may be presented in window 18. The artificial intelligence module may be based on machine learning concepts, as described in co-pending and commonly assigned U.S. patent application Ser. No. 16/512,751, the entirety of which is hereby incorporated by reference, and preferably is configured to provide an overlay one or more of the real time video image, image of the 3D model or 2D flat image.

Figure 2:
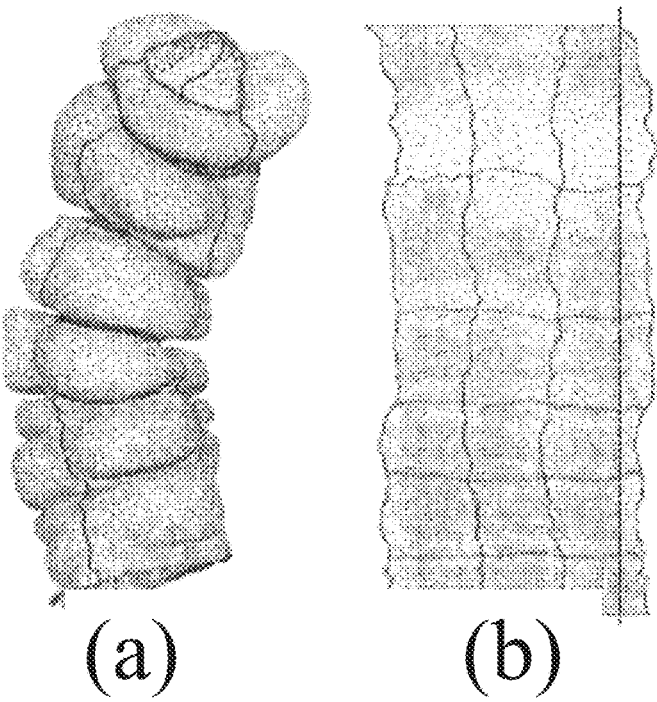
FIG. 2 is an illustrative image of a 3D model and a corresponding 2D flat image of the interior of a colon suitable for use in the system of the present invention.

Referring now to FIGS. 2a and 2b, an illustrative image of the 3D model reconstruction and 2D flat image of a colon are described. FIG. 2a shows an illustrative example of a 3D model of a patient's colon created by stitching together increments of the image stream received from the colonoscope camera, as described below. FIG. 2b is an illustrative example created by virtually slicing open the 3D model of FIG. 2a, unrolling it from a tubular configuration, and then stretching it to flatten tissue folds, resulting in a flat elongated 2-dimensional surface of the features of the interior surface of the colon. Preferably, the image of FIG. 2b is a bijective conformal map of the interior surface of the 3D model and thus retains registration with the 3D model. In this way, the endoscopist using, for example a touchscreen displaying the image of the 3D model, may locate a specific region in the 2D flat image. In accordance with one aspect of the invention, the 3D model and 2D image are generated incrementally as the tip of colonoscope is translated through the colon by the endoscopist, so as to provide a real time or near real time image. Further, in accordance with the invention, the 3D model and 2D image may be recorded and stored in an archive for retrieval and comparison during a subsequent procedure.

Figure 3:
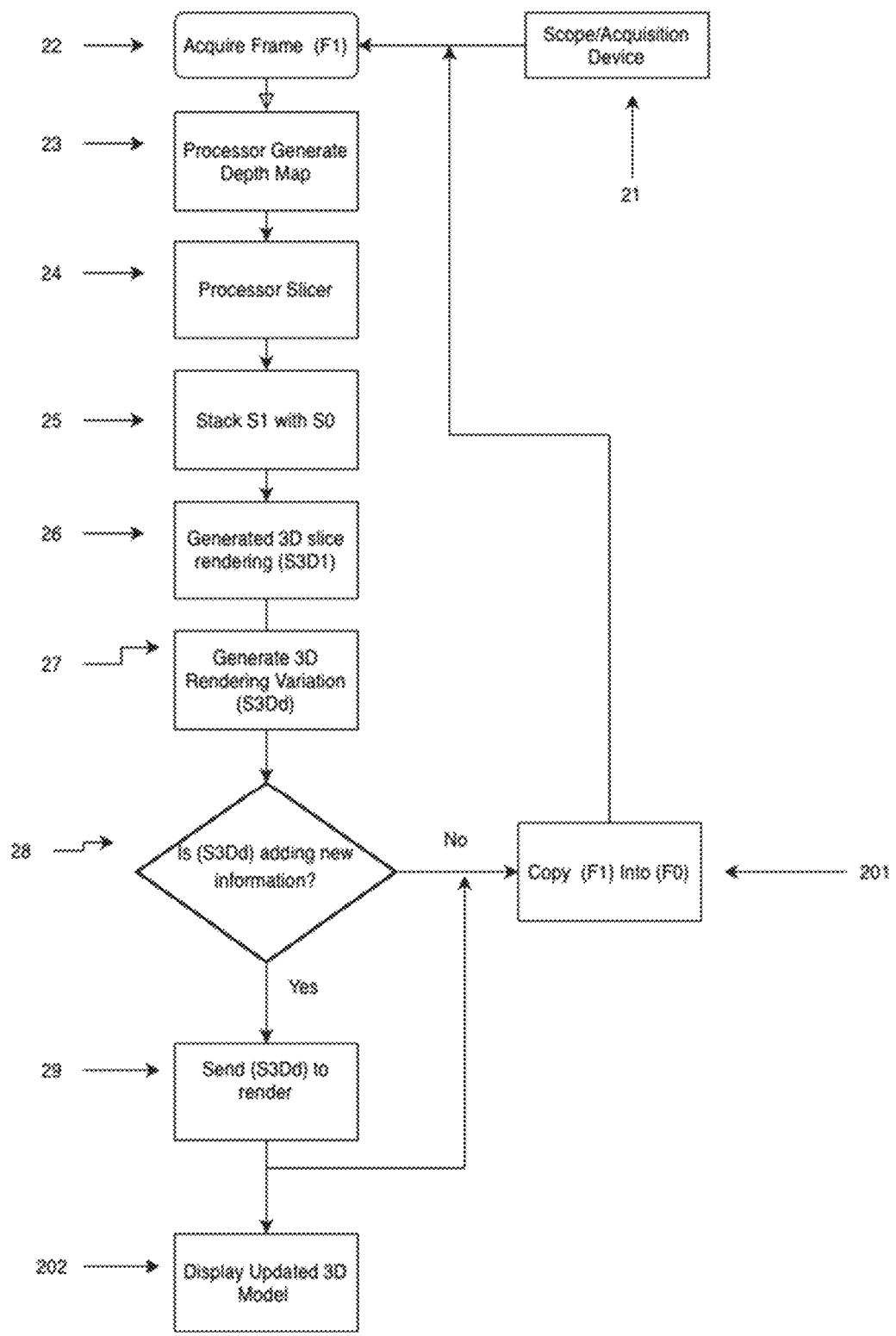
FIG. 3 is a flowchart of data processing in an embodiment of the inventive system.

In FIG. 3, an exemplary method of constructing a 3D model of a patient's colon using the video stream generated of the system of FIG. 1 is described, in which video frames generated at step 21 by a colonoscope disposed within patient P are provided to computer 12. In particular each video frame F1 from the live video stream is acquired at step 22. Frame F1 is analyzed using computer 12 to create a depth map, at step 23. The depth map preferably includes visual proximity data indicating the distance between the imaged anatomy and the plane of the endoscope camera lens.

At step 24, the depth map is sliced, so that only image pixels for tissue closest to the plane of the endoscope camera lens are used. The slicing depth preferably is set at a predetermined distance from the camera lens, and directly correlates with the longitudinal resolution of the 3D model being reconstructed. In a preferred embodiment, the depth map may be generated using a neural network processor that convolves the frames and generates a map of the distance to the endoscope camera lens plane. The depth slice then is correlated with frame F1 for texturing and slice $S_0$ of the colon is created with spatial and texture information of that visible portion of the colon.

At step 25, as the colonoscope is translated, additional frames and slices are generated, with each succeeding slice Si stacked with the previous slices $S_0$. In this manner, a 3D model of the colon, referred to as S3D1, can be constructed and then rendered for display to the endoscopist at step 26. At step 27, reconstruction S3D1 is further processed to compute a variation between a current 3D model of the colon and additional information provided by slice included in the most recent 3D model, referred to as S3Dd. At step 28, if S3Dd is different, for example, if it provides new information relating to a new longitudinal segment or feature of the interior surface not present in the preceding slice, the 3D model of the colon is updated at step 29, otherwise S3Dd is discarded. Additionally, specific anatomical features may be extracted and incorporated into S3Dd to optimize rendering of the variation analysis at step 27. 3D model rendering software in the display module then computes an incremental 3D rendering, at step 29, and at step 202, displays the image of that model in window 18 of display 16.

As the colonoscope moves inside the anatomy, computer 12 computes and compares each frame with the previous frame to determine if a new component of the anatomy has entered the field of view (FOV). If such a change is detected, a new image of the 3D model is rendering as each incremental component is added to the 3D model. As the colonoscope moves forward or backwards through the anatomy, the above process is repeated and the 3D model and rendered image is continually updated until the procedure is completed.

In a preferred embodiment, the navigation module may employ landmarks, e.g., tissue folds or angulations in the colon identified by the artificial intelligence module, to provide registration of images between frames. Other anatomical features, such as blood vessels, polyps, and ulcers or scars also may be used for this purpose. These landmarks also may be used at step 27 to determine if a new slice adds additional information to the 3D model.

The method of FIG. 3, when programmed in software, make also include a feature that enables an endoscopist to mark or highlight regions of the anatomy, for example, using an input device connected to computer 12 or a touchscreen feature of monitor 16, to retain those annotations for future reference and/or comparison. Any manually annotated features or features detected at step 27 also may be used to compute additional model segments S3Dd when computing frame differences at step 28.

In addition to the foregoing construction of the 3D model, computer 12 also may include a conformal mapping module to compute an unrolled 2D flat image of the interior surface of the colon from the video stream, as described for example in U.S. Pat. No. 6,697,538, which is incorporated herein by reference in its entirety. That patent describes how to generate a flattened conformal map from a digitized image. By tracking and using common video frames, slices and slice variations in both the 3D model and 2D flat image, bijective registration between those displays may be maintained, thereby enabling the endoscopist to use or switch between the image of the 3D model and 2D flat image to conduct a thorough procedure. In addition, because the 2D flat image may render certain areas, such as those located on tissue folds, more visible than the real time video image or image of the 3D model, it may focus the endoscopist's attention on areas that may otherwise be missed. Further, the artificial intelligence module also may be used to analyze 2D flat image, as well as the real time video image, to generate an additional overlay in the 2D flat image of potential polyps and/or adenomas.

Figure 4:
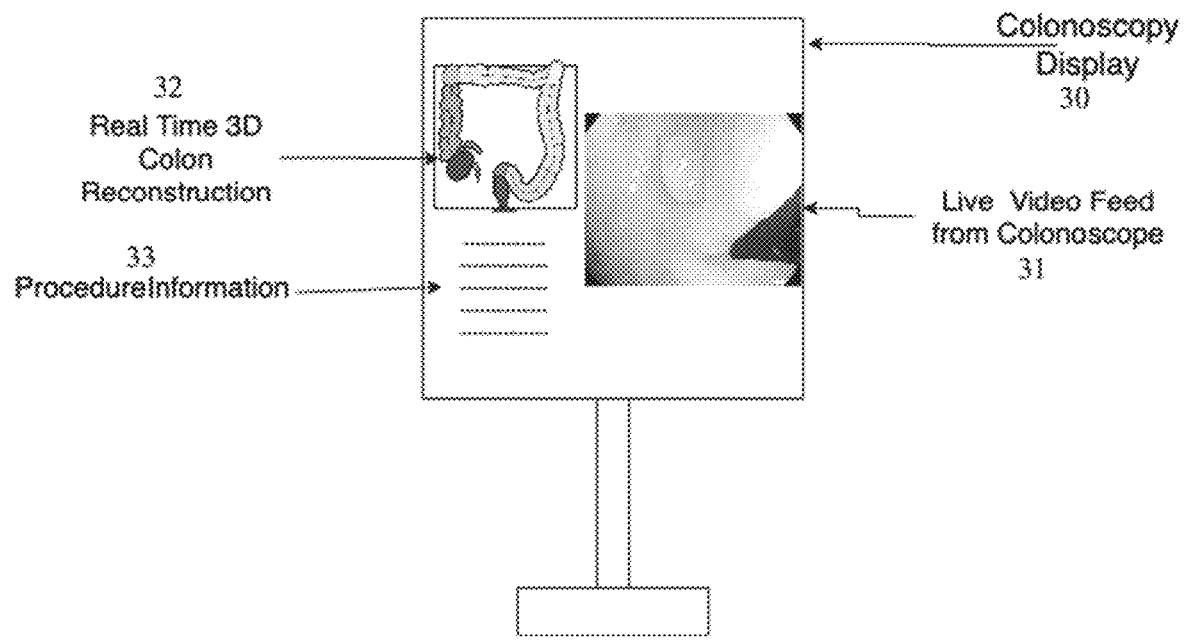
FIG. 4 is an embodiment of a display employed in the present invention.

Referring now to FIG. 4, colonoscopy display 30 includes windows 31 and 32. Windows 31 and 32 may be positioned on a single display device, or a plurality of display devices. Illustratively, the live video feed from the endoscope is presented in window 31, while the near real time 3D reconstruction of the colon is presented in window 32. As the endoscopist performs the procedure, window 31 is updated in real time. In a preferred embodiment, the image of the 3D model presented in window 32 is updated in real time or near real time, and optionally may display the location of the colonoscope tip overlaid on the image of the 3D model. In an alternative embodiment, window 32 may also present the 2D flat image of the interior surface of the colon in addition to the image of the 3D model.

Colonoscopy display 30, in addition, may include area 33 that contains patient information, annotation and messaging that is pertinent to the procedure. This information also may display navigational and directional information about the position of the colonoscope and/or suggestions regarding how to manipulate the colonoscope to capture views of the colon interior required to complete the 3D model and/or 2D flat image. Additional procedure information presented in area 33 may include relevant patient history, demographics, and quality measures of the colonoscopy procedure such as time of insertion.

In an alternative embodiment, a proximity sensor may be included in the distal end of the endoscope, e.g., near the endoscope tip. A signal output by the proximity sensor may be used to determine a distance between the longitudinal axis of the endoscope (or other reference point) and the texture of a specific point in space.

Figure 5:
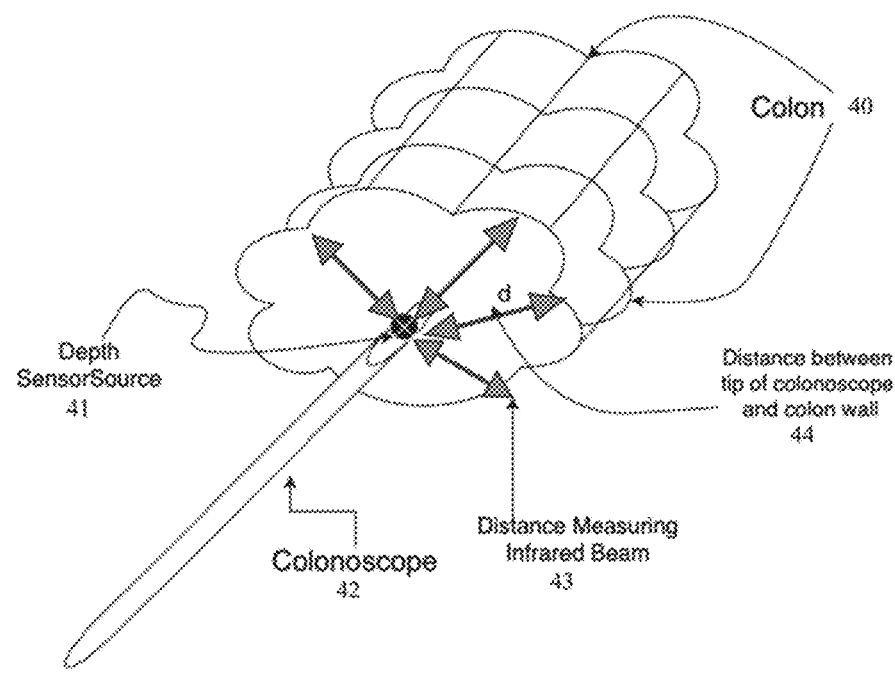
FIG. 5 is an illustrative embodiment of the system of the present invention in which a proximity sensor is employed to estimate 3D location of the endoscope tip in space.

Referring now to FIG. 5, an embodiment of an exemplary colonoscope having a proximity sensor for gathering additional information for construction of a 3D model is described. As shown in FIG. 5, a distal end of colonoscope 42 is disposed within a patient's colon. Infrared depth sensor 41 is disposed near the tip of colonoscope 42 and permits determination of the distance between the tip of the colonoscope and the colon wall.

In a preferred embodiment, depth sensor 42 emits infrared light beam 43 orthogonal to longitudinal axis of colonoscope 42; the sensor periodically rotates 360 degrees along its axis. The infrared beam impinges on interior 44 of the colon wall and returns with a certain delay and intensity to a detector located inside depth sensor 42. The delay and light intensity may be correlated to the distance between the infrared source and the colon wall. The determination of distance from a reflected light source for a close object may be performed using any of several methods known to persons of ordinary skill in the art, including, for example, timing of signal reflection and laser interferometry. In this way, an image of the interior surface of the colon wall may be created from successive measurements of distance between the colonoscopy tip and wall 44 of the colon, around the circumference of the colonoscope tip.

The resolution of the colon image slice generated using sensor 42 depends directly on the time and angular frequency of the distance measurements. As the tip moves longitudinally in the colon, that is, advances or retracts, the computer software incrementally creates an image of the colon from successive slices. In a preferred embodiment, the software in the computer assesses the degree of overlap of each slice to assess a longitudinal distance between the slices.

As noted above, one challenge of constructing a 3D model of an organ such as a colon is that the shape of the organ is not static, but instead, the organ moves naturally, for example, due to peristalsis or as a result of the colonoscopy procedure itself. This makes comparison of 3D models obtained at different times particularly challenging. However, this drawback is overcome in the inventive system by unrolling and flattening the interior surface of the organ being imaged to create the 2D flat display (with appropriate and necessary geometric distortion), as described above. In this way, missing areas of the internal surface can be highlighted, which draws the attention of the endoscopist to return to the missing areas and fill in the gaps by further examination.

In accordance with a further feature of the present invention, an optional storage and indexing model records and stores the 3D model and 2D flat image generated during a procedure and associates that data with the patient's medical record. When the patient returns for a later follow-up endoscopy, the 3D model and 2D flat image may be recalled and presented to the endoscopist for comparison, to allow the endoscopist the ability to observe changes that occurred during the intervening period, either directly or with the assistance of the artificial intelligence module. The temporal information thus generated is expected to aid the physician in determining if there have been changes in the image such as recurrence of a polyp.

Figure 6:
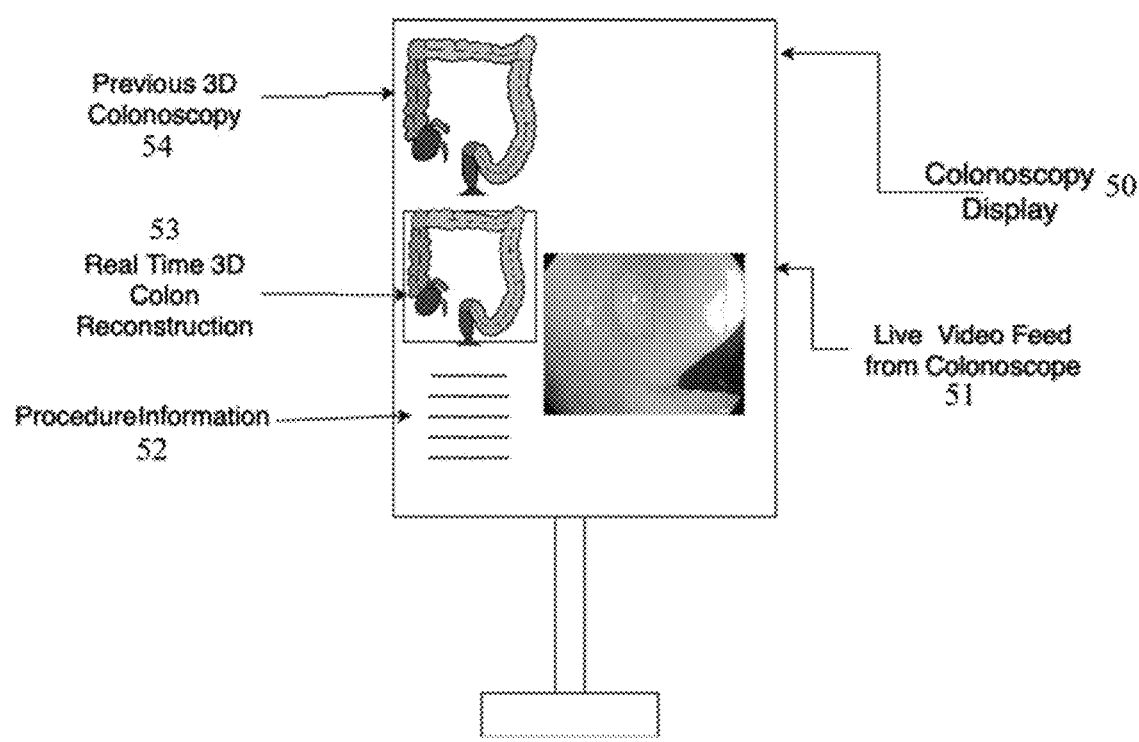
FIG. 6 is an exemplary embodiment of a display that provides temporal information.

FIG. 6 provides an illustration how the inventive system may be used with temporal information to aid an endoscopist while performing a follow-up procedure. Colonoscopy display 50 presents information and images and may be a single display monitor or a plurality of display monitors. Window 51 displays a live video feed from a colonoscope. In a preferred embodiment, window 51 also presents information about the presence of polyps determined by the artificial intelligence module. Window 53 displays the real-time incremental image of the 3D model and/or 2D flat image of the colon. Preferably, the position of the tip of the colonoscope also is indicated in window 53, for example, as an overlay on the image of the 3D model and/or 2D flat image to aid in navigation.

Window 54 displays the image of the 3D model and/or 2D flat image of the patient's colon from a previous procedure, for example, as retrieved by the storage and indexing module from mass storage device 15. The display module preferably orients the previous images to the same orientation as the present images. Additional information about the procedure also may be presented in window 52. As discussed above, the artificial intelligence module may compare the prior 3D model and/or 2D flat image from the previous procedure to the current 3D model and/or 2D flat image from the current procedure to highlight differences for the endoscopist's consideration.

Various general-purpose systems may be used to implement the systems and methods in accordance with the teachings herein. Alternatively, the system made be implemented with more specialized apparatus. Implementation of the inventive features is not limited to any particular endoscope manufacturer, ancillary endoscopy equipment, programming languages, or computer systems. It will be appreciated that a variety of commercially available endoscopy equipment, networking methods, and programming languages may be used to implement the inventive systems and methods.

The system and methods described herein may be provided as a computer program product, or software, that may include a machine-readable medium having stored thereon instructions, which may be used to program a computer system (or other electronic devices) to perform a process according to the present disclosure. A machine-readable medium includes any medium for storing information in a form readable by a machine (e.g., a computer). For example, a machine-readable (e.g., computer-readable) medium includes a machine readable storage medium such as a read only memory ("ROM"), random access memory ("RAM"), magnetic disk storage media, optical storage media, flash memory devices, etc.

It will also be appreciated by one skilled in the art than any data or program storage could be cloud storage, accessible via internet connection such as wireless (Wi-Fi), fixed line (Ethernet) or via the data service on a mobile network.

In addition it should be understood that steps of the exemplary methods set forth herein may be performed in different orders than presented in this specification. Furthermore, some steps of the exemplary methods may be performed in parallel rather than sequentially. The steps of the exemplary methods may be performed in any suitable location including a hospital, ambulatory surgery center, outpatient clinic, doctor's office, or a mobile facility.

In the foregoing disclosure, embodiments have been described with reference to specific example implementations thereof. It will be evident that various modifications may be made thereto without departing from the broader spirit and scope of the disclosure as set forth in the following claims.

What is claimed is:

1. A system for enhancing abnormality detected by an endoscopist during an endoscopic procedure, the system comprising:
    an endoscopy system having an endoscope including a lens, the endoscopy system configured to output a video stream of an interior surface of an organ;
    a monitor having a first window;
    an electronic memory having instructions stored therein, the instructions including a 3D reconstruction module and a display module; and
    a processor operationally coupled to the endoscopy system and the monitor, the processor configured to access the electronic memory and execute the instructions stored therein such that:
        the 3D reconstruction module:
            analyzes frames of the video stream to generate slices, each slice capturing only image pixels corresponding to an image plane disposed a predetermined incremental depth from the lens; and
            concatenates adjacent consecutive slices to generate in, at least near real time, a 3D model of the interior surface; and
        the display module renders an image of the 3D model for viewing in the first window,
    wherein the image facilitates navigation of the endoscope by the endoscopist within the organ.

2. The system of claim 1, wherein the instructions stored in the electronic memory further comprises a navigation module and the processor further is configured to execute the navigation module to generate navigational indicia for the endoscopist, the navigational indicia overlaid on the image of the 3D model rendered by the display module.

3. The system of claim 1, wherein the monitor includes a second window that displays the video stream of the interior surface of an organ, the instructions stored in the electronic memory further comprises an artificial intelligence module, and the processor further is configured to execute the artificial intelligence module to search for features in the video stream indicative of tissue abnormalities and to generate an overlay for display in the second window indicative of a presence of tissue abnormalities.

4. The system of claim 1, wherein the monitor includes a third window, the instructions stored in the electronic memory further comprises a conformal mapping module and the processor further is configured to execute the conformal mapping module to generate a 2D flat image of the interior surface of the organ, and wherein the display module is configured to display the 2D flat image in the third window.

5. The system of claim 4, wherein the artificial intelligence module is configured to search for features in the 2D flat image indicative of tissue abnormalities and to generate an overlay for display in the third window indicative of a presence of tissue abnormalities.

6. The system of claim 1, wherein 3D reconstruction model and conformal mapping modules provide bijective correspondence between the 3D model and 2D flat image.

7. The system of claim 1, wherein the monitor includes a fourth window for displaying patient specific information.

8. The system of claim 1, further comprising a mass storage device operationally coupled to the processor, wherein the instructions stored in the electronic memory further comprise a storage and indexing module configured for storing the 3D model in the mass storage device at a conclusion of the endoscopic procedure.

9. The system of claim 3, further comprising a mass storage device operationally coupled to the processor, wherein the instructions stored in the electronic memory further comprise a storage and indexing module configured for storing the 3D model in the mass storage device at a conclusion of the endoscopic procedure.

10. The system of claim 9, wherein the artificial intelligence module further is configured to retrieve a prior 3D model from a previous endoscopic procedure, compare the prior 3D model to a current 3D model generated during a current endoscopic procedure, and generate for display in the first window an overlay highlighting differences between the prior 3D model and the current 3D model.

11. A system for enhancing abnormality detected by an endoscopist during an endoscopic procedure, the system comprising:
    an endoscopy system having an endoscope including a lens, the endoscopy system configured to output a video stream of an interior surface of an organ;
    a monitor having first and second windows;
    an electronic memory having instructions stored therein, the instructions including a 3D reconstruction module, a conformal mapping module and a display module; and
    a processor operationally coupled to the endoscopy system and the monitor, the processor configured to access the electronic memory and execute the instructions stored therein such that:
        the 3D reconstruction module:
            analyzes frames of the video stream to generate slices, each slice capturing only image pixels corresponding to an image plane disposed a predetermined incremental depth from the lens; and
concatenates adjacent consecutive slices to generate in, at least near real time, a 3D model of the interior surface;

the conformal mapping module analyzes the video stream to generate a 2D flat image of the interior surface, and the display module renders an image of the 3D model for viewing in the first window and the displays the 2D flat image in the second window, wherein at least one of the image or 2D flat image facilitates navigation of the endoscope by the endoscopist within the organ.

12. The system of claim 11, wherein the instructions stored in the electronic memory further comprises a navigation module and the processor further is configured to execute the navigation module to generate navigational indicia for the endoscopist, the navigational indicia overlaid on the image of the 3D model rendered by the display module.

13. The system of claim 11, wherein the instructions stored in the electronic memory further comprises a navigation module and the processor further is configured to execute the navigation module to generate navigational indicia for the endoscopist, the navigational indicia overlaid on the image of the 2D flat image displayed by the display module.

14. The system of claim 11, wherein the monitor includes a third window that displays the video stream of the interior surface of an organ, the instructions stored in the electronic memory further comprises an artificial intelligence module, and the processor further is configured to execute the artificial intelligence module to search for features in the video stream indicative of tissue abnormalities and to generate an overlay for display in the third window indicative of a presence of tissue abnormalities.

15. The system of claim 14, wherein the artificial intelligence module is configured to search for features in the 2D flat image indicative of tissue abnormalities and to generate an overlay for display in the second window indicative of a presence of tissue abnormalities.

16. The system of claim 11, wherein 3D reconstruction model and conformal mapping modules provide bijective correspondence between the 3D model and 2D flat image.

17. The system of claim 11, wherein the monitor includes a fourth window for displaying patient specific information.

18. The system of claim 11, further comprising a mass storage device operationally coupled to the processor, wherein the instructions stored in the electronic memory further comprise a storage and indexing module configured for storing the 3D model and 2D flat image in the mass storage device at a conclusion of the endoscopic procedure.

19. The system of claim 14, further comprising a mass storage device operationally coupled to the processor, wherein the instructions stored in the electronic memory further comprise a storage and indexing module configured for storing the 3D model and 2D flat image in the mass storage device at a conclusion of the endoscopic procedure.

20. The system of claim 19, wherein the artificial intelligence module further is configured to retrieve a prior 2D flat image from a previous endoscopic procedure, compare the prior 2D flat image to a current 2D flat image generated during a current endoscopic procedure, and generate for display in the second window an overlay highlighting differences between the prior 2D flat image and the current 2D flat image.

* * * * *